(12) United States Patent
Li et al.

(10) Patent No.: US 6,805,878 B2
(45) Date of Patent: Oct. 19, 2004

(54) TRANSDERMAL ADMINISTRATION OF ACE INHIBITORS

(75) Inventors: Chensheng Li, Miami, FL (US); Viet Nguyen, Miami, FL (US)

(73) Assignee: Noven Pharmaceuticals, Inc., Miami, FL (US)

( * ) Notice: Subject to any disclaimer, the term of this patent is extended or adjusted under 35 U.S.C. 154(b) by 0 days.

(21) Appl. No.: 10/014,785

(22) Filed: Dec. 14, 2001

(65) Prior Publication Data

US 2003/0064933 A1 Apr. 3, 2003

Related U.S. Application Data

(60) Provisional application No. 60/318,632, filed on Sep. 13, 2001.

(51) Int. Cl.[7] ............ A61F 13/00; A61F 13/02; A61L 15/16
(52) U.S. Cl. ............ 424/449; 424/448; 424/443
(58) Field of Search ................ 424/449, 448, 424/443

(56) References Cited

U.S. PATENT DOCUMENTS

| | | | |
|---|---|---|---|
| 4,213,978 A | 7/1980 | Bodor et al. | |
| 4,847,250 A | 7/1989 | Alexander et al. | |
| 5,474,783 A | 12/1995 | Miranda et al. | |
| 5,622,944 A | 4/1997 | Hale et al. | |
| 5,656,285 A | 8/1997 | Sablotsky et al. | |
| 5,656,286 A | 8/1997 | Miranda et al. | |
| 5,925,372 A | 7/1999 | Berner et al. | |
| 5,948,434 A | 9/1999 | Labrie | |
| 6,024,976 A | 2/2000 | Miranda et al. | |
| 6,277,892 B1 | 8/2001 | Deckner et al. | |
| 6,303,141 B1 | 10/2001 | Fischer et al. | |
| 6,387,894 B1 * | 5/2002 | Fossa .............. | 514/212.07 |
| 2002/0004065 A1 * | 1/2002 | Kanios .............. | 424/449 |

FOREIGN PATENT DOCUMENTS

| | | |
|---|---|---|
| EP | 0 458 641 A2 | 5/1991 |
| EP | 0 439 430 A2 | 7/1991 |
| EP | 0 468 875 B1 | 1/1992 |
| EP | 0 581 587 A2 | 7/1993 |
| WO | WO 93/23019 A1 | 11/1993 |
| WO | WO 99/42111 A1 | 8/1999 |
| WO | WO 00/66104 A2 | 11/2000 |
| WO | WO 02/03970 A2 | 1/2002 |

OTHER PUBLICATIONS

Nicolas Bodor, Jack Zupan and Sally Selk; *Improved Delivery Through Biological Membranes Vii. Dermal Delivery of Cromoglycic Acid (Cromolyn) Via Its Prodrugs*; International Journal of Pharmaceutics, (Nov. 1980); vol. 7, No. 1; pp. 63–75; Elsevier/North–Holland Biomedical Press; The Netherlands.

C. Desbonnet, A.H. Kennedy, S.C. McNeill, E. Wakshull, R.O. Potts; "Abstract for" *Transdermal Drug Transport and Metabolism Are Correlated*; Clinical Research; (Apr. 1988); pp. 640A; vol. 36, No. 3; The American Federation for Clinical Research; Washington, D.C.

(List continued on next page.)

Primary Examiner—Thurman K. Page
Assistant Examiner—Isis Ghali
(74) Attorney, Agent, or Firm—Foley & Lardner LLP

(57) ABSTRACT

Disclosed is a dermal composition comprising enalapril ethyl ester or another prodrug corresponding to a pharmaceutically active form of an ACE inhibitor in an amount corresponding to a therapeutically effective amount of enalaprilat (or other pharmaceutically active form of enalapri) or pharmaceutically active form of the ACE inhibitor in admixture with a pharmaceutically acceptable carrier. In a preferred embodiment, the carrier is a pressure-sensitive adhesive matrix comprising a polymer or polymer blend. The dermal composition is applied in a method of substantially increasing the flux of enalaprilat through the skin of a human or an animal by maintaining the dermal composition in contact with the skin.

8 Claims, 2 Drawing Sheets

OTHER PUBLICATIONS

Milind M. Narurkar and Ashim K. Mitra; "Abstract for" *Improved Ocular Delivery of idoxuridine Using The Prodrug Approach*; Pharmaceutical Research–Official Journal of the American Association of Pharmaceutical Scientists; (Oct. 1988); vol. 5, No. 10; pp. S–98/PD 904; Plenum Press, New York and London.

Fort, James Joseph, Ph.D. and Ashim K. Mitra; *Investigation Of A Series Of Methotrexate Dialkyl Esters As Potential Prodrugs For Topical Delivery*; Dissertation Abstracts International–B The Sciences and Engineering; Health Sciences, Pharmacy; (May 1990); pp. 5005–B; vol. 50, No. II; U–M–I.

Beall, Howard D., Ph.D. and K.B. Sloan; *Bioreversible Derivatives Of 5–Fluorouracil (5FU): Improving Dermal And Transdermal Delivery With Prodrugs*; Dissertation Abstracts International–B The Sciences and Engineering; Chemistry, Pharmaceutical; (Aug. 1992); pp. 859–B; vol. 53, No. 2; U–M–I.

Hiroto Bando, Mikiko Sahashi, Toshihide Takagi, Fumiyoshi Yamashita, Yoshinobu Takakura, Mitsuru Hashida; *Analysis Of In Vitro Skin Penetration Of Acyclovir Prodrugs Based On A Diffusion Model With A Metabolic Process*; International Journal of Pharmaceutics; (Jun. 17, 1996); pp. 91–102; vol. 135, Nos. 1 and 2; Elsevier Science B.V.

Hiroto Bando, Mikiko Sahashi, Saya Mohri, Fumiyoshi Yamashita, Yoshinobu Takakura, Mitsuru Hashida; *In Vivo Skin Penetration Enhancement Of Acyclovir By Theoretical Design Of Prodrug–Enhancer Combination*; International Journal of Pharmaceutics; (Dec. 6, 1996); pp. 103–113; vol. 145, NOs. 1 and 2; Elsevier Science B.V.

Hiroto Bando, Mikiko Sahashi, Fumiyoshi Yamashita, Yoshinobu Takakura, Mitsuru Hashida; *In Vivo Evaluation of Acyclovir Prodrug Penetration and Metabolism Through Rat Skin Using a Diffusion/Bioconversion Model*; Pharmaceutical Research; Journal of Pharmaceutical Sciences; (Jun. 1997); pp. 56–62; vol. 86, No. 6; American Pharmaceutical Association and the American Chemical Society, United States of America.

G.C. Santus and R.W. Baker; *Transdermal Enhancer Patient Literature*; Journal of Controlled Release; (1993); pp. 1–20; vol. 25; Elsevier Science Publishers B.V.

Hiroto Bando, Saya Mohri, Fumiyoshi Yamashita, Yoshinobu Takakura, and Mitsuru Hashida; *Effects of Skin Metabolism on Percutaneous Penetration of Lipophilic Drugs*; Journal of Pharmaceutical Sciences; (Jun. 1997); pp. 759–761; vol. 86, No. 6; The American Chemical Society and American Pharmaceutical Association.

Gillian P. McMahon, Shane J. O'Connor, Desmond J. Fitzgerald, Sylvie le Roy, Mary T. Kelly; *Determination of Aspirin and Salicylic Acid in Transdermal Perfusates*; Journal of Chromatography B; (Apr. 10, 1998); pp. 322–327; vol. 707, Nos. 1 and 2; Elsevier Science B.V.

H. Bundgaard; *Design and Application of Prodrugs*; A Textbook of Drug Design and Development; (1991); pp. 113–191; Chapter 5; Harwood Academic Publishers, Switzerland.

Eugene R. Cooper; *Increased Skin Permeability for Lipophilic Molecules*; Journal of Pharmaceutical Sciences; (Aug. 1984); pp. 1153–1156; vol. 73, No. 8; American Pharmaceutical Association, United States of America.

T. Loftsson, *Effects of Cyclodextrins and Polymers on Transdermal Drug DeliveryProceed. Intern. Symp. Control. Ref., Bioact. Mater.*, (1996), pp. 194–195., 23, Control Release Society, Inc.

Li et al., "The Study of Transdermal Administration of ACE Inhibitors and Improved Absorption of Their Prodrugs", Noven Pharmaceuticals, Inc., Nov. 2, 2000 (2 pgs).

* cited by examiner

Enalapril: Ethyl Ester vs. Maleate

Enalapril Ester Flux

TRANSDERMAL ADMINISTRATION OF ACE INHIBITORS

RELATED APPLICATIONS

This application claims priority to provisional patent application No. 60/318,632, filed Sep. 13, 2001.

BACKGROUND OF THE INVENTION

The present invention relates to transdermal drug delivery systems. More particularly, the present invention relates to transdermal drug delivery systems for delivering pharmaceutically effective amounts of ACE inhibitors, preferably enalaprilat, and to methods of making and using the same.

The use of a transdermal drug delivery system, for example a pressure-sensitive adhesive containing a medicament, namely, a drug, as a means for administering therapeutically effective amounts of the medicament is well known. Such known delivery systems involve incorporation of a medicament into a carrier such as a polymeric and/or a pressure-sensitive adhesive formulation or other forms of carriers. The pressure-sensitive adhesive must adhere effectively to the skin and permit migration of the medicament from the carrier through the skin and into the bloodstream of the patient. The delivery system is an effective means for introducing drugs into the blood stream by applying a patch to skin. The major penetration pathway of drug molecules through the stratum corneum of intact human skin is by diffusion of the drug through the lipid envelopes of the skin cells.

The use of transdermal drug delivery systems for some drug classes is disclosed in the art. For example, steroids such as estradiol and norethindrone are especially well known for use in transdermal drug delivery systems, in particular, as hormone replacement therapy. See U.S. Pat. Nos. 6,221,383 and 5,474,783, both of which are assigned to Noven Pharmaceuticals, Inc. of Miami, Fla. Lipophilic prodrugs of other pharmaceutically active agents such as the anti-asthmatic cromolyn (Bodor et al, *International Journal of Pharmaceutics* 7 (1980) 63–75), anti-neoplastic fluorouracil (Beall, *Dissertation Abstracts International* 53 (1992) 859-B), anti-psoriatic methotrexate (Fort, *Dissertation Abstracts International* 50 (1 990) 5005-B), and anti-herpes drug idoxuridine (Narurkar et al, *Pharmaceutical Research* 5 (1988) S-98) have been studied with respect to transdermal drug delivery systems.

One problem typically encountered in the development of transdermal drug delivery systems is the polarity of parent drugs, such as those mentioned above, which can significantly attenuate the rate of drug delivery (commonly called "flux" or "permeation rate") from a transdermal drug delivery system. One promising solution to this problem, as implicated in the above-referenced art, focuses on the administration of lipophilic prodrugs that exhibit somewhat enhanced penetration of skin. Conversion of a lipophilic simple ester prodrug, for example, back into the polar and hydrophilic parent carboxyl-containing drug typically occurs via enzymatic reactions in the skin, Accordingly, prodrugs which are too small (e.g., of low molecular weight) may pass quickly through the skin and would thus not persist long enough in the skin to be transformed back into the parent drugs. Despite these complications, circumstances wherein therapeutic levels of a drug can be successfully attained via transdermal administration offer a number of desirable advantages of this route over other routes of drug administration. Transdermal administration of a drug is often convenient and comfortable for a patient. Control of flux with a single continuous application allows delivery of a sufficiently therapeutic yet non-toxic level of a drug. In contrast, oral administration of many drugs is sometimes unfeasible in view of significant drug decomposition in the gastrointestinal tract, lack of absorption from the gastrointestinal tract, and gastrointestinal upset or damage. Transdermal delivery of a drug also by-passes the first phase of hepatic metabolism, thereby lowering the overall minimum required dosage of the drug to achieve therapeutic levels.

In view of the limited number of drugs administered transdermally, there are applications where it is desirable to administer other drugs percutaneously instead of, for example, orally or intravenously. One class of drugs hitherto believed to be unsuitable for transdermal delivery is the group of angiotensin-converting enzyme ("ACE") inhibitors that have become the first-line therapy in treating hypertensive patients. Most ACE inhibitors are bi-peptides that are too hydrophilic to penetrate the lipid layers of skin and are accordingly administered orally, intravenously, or both. The well-known ACE inhibitor enalaprilat is an effective drug for use in the treatment of hypertension and heart failure, and would thus be advantageously administered percutaneously to benefit a patient for the reasons discussed above. See Jackson et al in, "Goodman and Gilman's, The Pharmacological Basis of Therapeutics, Ninth Edition", pp. 733–758, (J. G. Hardman, L. E. Limbird, P. D. Molinoff, R. W. Ruddon, A. G. Gilman, eds.), McGraw Hill, New York (1996) and Oates in, "Goodman and Gilman's, The Pharmacological Basis of Therapeutics, Ninth Edition", pp. 780–808, (J. G. Hardman, L. E. Limbird, P. D. Molinoff, R. W. Ruddon, A. G. Gilman, eds.), McGraw Hill, New York (1996). However, enaliprilat is a polar compound because it bears two carboxylic acid moieties in its structure, and therefore exhibits very low flux through skin. Likewise, the orally administered form of enalaprilat—enalapril maleate—is also too polar for efficacious transdermal drug delivery. Despite this drawback, it is believed that the advantageous size (i.e., molecular weight) and attainable therapeutic dosage of enalaprilat present it as an attractive candidate for use in transdermal drug delivery systems. For the foregoing reasons, other ACE inhibitors that share these structural and chemical features with enalapril would also be useful in transdermal drug delivery systems. Thus, it would be desirable to administer to a patient a dermal composition of enalaprilat or enalapril or other pharmaceutically active form of ACE inhibitors in a form suitable for use in transdermal drug delivery systems.

SUMMARY OF THE INVENTION

One object of the present invention is to provide a dermal composition that is able to deliver a therapeutically effective amount of a pharmaceutically active form ("the drug") of an ACE inhibitor selected from the group consisting of enalapril, benazepril, lisinopril, perindopril, quinapril, ramipril, spirapril, temocapril, or trandolapril. Another object of the present invention is to provide a dermal composition of a prodrug of the drug. Yet another object is to provide a transdermal drug delivery system that has a substantially improved flux of the prodrug of the drug compared to that of a system of equal size that employs a more polar derivative of the drug.

In accomplishing the foregoing and other objects, there has been provided according to one aspect of the present invention a dermal composition comprising the prodrug enalapril ethyl ester (shown below) in an amount corresponding to a therapeutically effective amount of the pharmaceutically active drug enalaprilat (also shown below) or enalapril in admixture with a carrier. Other prodrugs contemplated for the dermal composition of the present invention include lipophilic prodrugs of pharmaceutically active forms of ACE inhibitors selected from benazepril, lisinopril, perindopril, quinapril, ramipril, spirapril, temocapril, or trandolapril. In one preferred embodiment, the carrier is a polymer that comprises a pressure-sensitive adhesive.

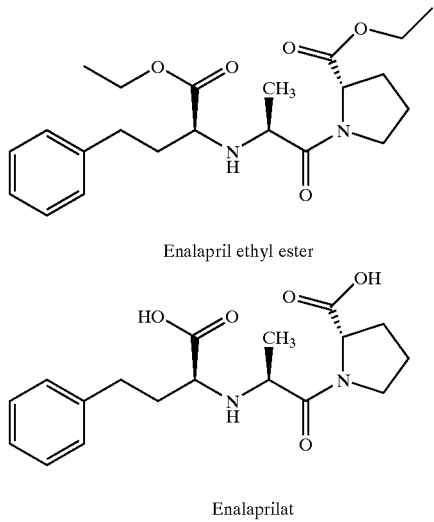

Enalapril ethyl ester

Enalaprilat

According to a second aspect of the present invention, there is provided a method of making a dermal composition described above that comprises converting the drug into a more lipophilic derivative ("prodrug") and forming a mixture of the so-formed prodrug and a carrier. Preferably, the carrier is a polymer and the method further comprises the steps of forming the mixture into a polymer matrix and drying the polymer matrix to remove volatile solvents to form the dermal composition.

According to a third aspect of the invention, there is provided a method of substantially increasing the flux of the drug through the skin of a human or an animal comprising the steps of applying to the skin of an animal or human being, the dermal composition described above, and maintaining the dermal composition in contact with the skin.

According to a fourth aspect of the invention, there is provided a method of treating a human or an animal in need of an angiotensin-converting enzyme ("ACE") inhibitor with a therapeutically effective amount of the drug, that comprises the steps of applying to the skin of the said animal or human being, the dermal composition described above; and maintaining the dermal composition in contact with the skin for a predetermined length of time sufficient to administer a therapeutically effective amount of the drug. This aspect of the present invention thus provides for the treatment of conditions such as hypertension, heart failure, myocardial infarction, and nephropathy.

DETAILED DESCRIPTION OF THE PREFERRED EMBODIMENTS

Figure 1:
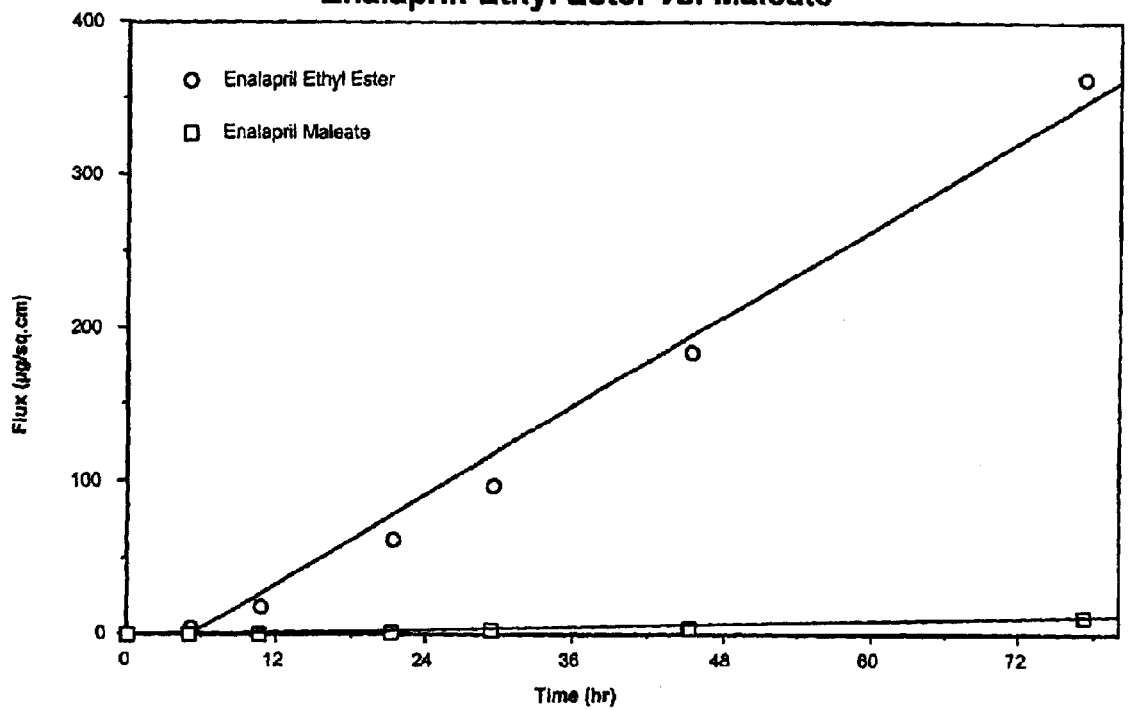
FIG. 1 is a graph illustrating the flux of a dermal composition containing enalapril maleate (shown as squares, "□") and of a dermal composition containing enalapril ethyl ester (shown as circles, "○").

The present invention provides, inter alia, a transdermal drug delivery composition for the administration of a therapeutically effective amount of enalaprilat or enalapril as its enalapril ethyl ester prodrug, and in particular, transdermal compositions of enalapril ethyl ester exhibiting a substantially greater flux than that of enalaprilat in its enalapril maleate form.

As used herein and understood by one of skill in the art, the term "prodrug" is a pharmaceutically less active chemical derivative of a drug molecule that requires transformation in vivo in order to release the pharmaceutically active drug. See Bundgaard, "Design and Application of Prodrugs", A Textbook of Drug Design and Development, pp. 112–191, (P. Krogsgaard-Larsen and H. Bundgaard, eds.), Harwood Academic Publishers, Pennsylvania (1991). As also used herein, a "pharmaceutically active form of the ACE inhibitor" also called "the drug" is the ACE inhibitor in its monoester form, or its more potent hydrolyzed or metabolized dicarboxylic acid form.

As used herein, "transdermal" delivery is intended to encompass both transdermal (or "percutaneous" or "dermal") and transmucosal administration; that is, delivery by passage of a drug through skin or mucosal tissue and into the bloodstream.

As used herein the term "flux" (also called "permeation rate") is defined as the absorption of a drug through skin or mucosal tissue, and is described by Fick's first law of diffusion:

$$J = -D(dCm/dx),$$

where J is the flux in $g/cm^2/sec$, D is the diffusion coefficient of the drug through the skin or mucosa in $cm^2/sec$ and dCm/dx is the concentration gradient of the drug across the skin or mucosa.

The present inventors have unexpectedly discovered that the flux of the polar drug enalaprilat in its enalapril maleate form through skin is negligible while that of the lipophilic enalapril ethyl ester prodrug is significantly greater. According to one aspect of the present invention, the increase in flux of the prodrug over that of the drug is determined by evaluating the ratio of the flux of the dermal composition containing enalapril ethyl ester to the flux of enalapril maleate under similar conditions. Preferably, the ratio is 100:1 to 3:1, more preferably 70:1 to 10:1, and even more preferably 30:1 to 20:1. For example, the inventors found that the flux of a dermal composition of enalapril ethyl ester is 4.8 $\mu g/cm^2/sec$ while that of enalapril maleate is 0.2 $\mu g/cm^2/sec$, thereby yielding a flux ratio of 24:1. See FIG. 1.

Without wishing to be bound by any particular theory, the inventors believe that the increased lipophilicity of enalapril ethyl ester relative to that of enalapril maleate greatly facilitates the entry of this prodrug into the stratum corneum of the intact skin of a subject where it is ultimately hydrolyzed into the pharmacologically active and more polar enalaprilat. The hydrolysis of the ester groups in enalapril ethyl ester to carboxyl groups in enalaprilat, in turn, accelerates the diffusion of enalaprilat through the skin and into the blood of the subject. That is, the reversible masking of one or more carboxyl groups on enalaprilat is achieved by preparing a simple ester form of enalaprilat and then using the skin of a subject as the mechanism to provide both transport and metabolism of the ester prodrug to enhance the permeation process.

Similarly pharmacologically active form of the ACE inhibitors benazepril, lisinopril, perindopril, quinapril, ramipril, spirapril, temocapril, and trandolapril all contain two carboxyl moieties that are converted to more lipophilic moieties. Preferably, the derivative is an ester, preferably a diester. Accordingly, it is believed that these lipophilic derivatives can also be hydrolyzed into their pharmacologically active forms upon transport through the skin of a patient.

Typically, the amount of the prodrug in the dermal composition can vary from about 1% to about 50% by weight. Preferably, the amount is from 5% to 30%, and most preferably is from 10% to 20%.

The prodrug is present in a carrier. The term "carrier" as used herein refers to carrier materials suitable for facilitating transdermal drug administration, and include any such materials known in the art, e.g., any liquid, gel, solvent, liquid diluent, solubilizer, polymer or the like, which is nontoxic and which does not significantly interact with other components of the composition or the skin in a deleterious manner. The carrier is present in an amount sufficient to achieve its function of carrying the prodrug. Preferably, the carrier is present in an amount ranging from 2 to 99 wt %, more preferably 30 to 90 wt %, even more preferably 40 to 80 wt %. The carrier is substantially free of water and preferably contains no water.

Particularly preferred carriers are flexible, finite systems. The phrase "flexible, finite system" is intended to mean a solid form capable of conforming to the surface with which it comes into contact, and which is capable of maintaining the contact in such solid form so as to facilitate topical application without adverse physiological response, and without being appreciably decomposed by aqueous contact during administration to a patient. Particularly preferred flexible, finite systems are polymer carriers such as the pressure-sensitive adhesive matrix type in which the prodrug is dispersed directly in the pressure-sensitive adhesive or reservoir type carriers.

Illustrative examples of suitable adhesives as matrix type flexible, finite delivery systems include those described in U.S. Pat. Nos. 5,474,783, and 5,656,386 both assigned to Noven Pharmaceuticals, Inc., Miami, Fla. (incorporated herein by reference in their entireties). Other flexible, finite systems known in the art include films, plasters, dressings, and bandages, as well as multilayer delivery systems in which the enalapril ethyl ester is solubilized or contained in one or more separate layers and reservoir-type delivery systems in which the enalapril ethyl ester is solubilized or contained in a reservoir or depot separate from the adhesive which attaches directly to the skin or mucosa.

As noted above, particularly preferred carriers are pressure-sensitive adhesive flexible, finite carriers. These can include any viscoelastic material which adheres instantaneously to most substrates with the application of very slight pressure and remains permanently tacky. A polymer is a pressure-sensitive adhesive within the meaning of the term as used herein if it has the properties of a pressure-sensitive adhesive per se or functions as a pressure-sensitive adhesive by admixture with tackifiers, plasticizers or other additives. The term "pressure-sensitive adhesive" also includes mixtures of different polymers and mixtures of polymers, such as polyisobutylenes (PIB), of different molecular weights, wherein each resultant mixture is a pressure-sensitive adhesive. Other useful rubber based pressure-sensitive adhesives include hydrocarbon polymers such as natural and synthetic polyisoprene, polybutylene and polyisobutylene, styrene/butadiene polymers styrene-isoprene-styrene block copolymers, hydrocarbon polymers such as butyl rubber, halogen-containing polymers such as polyacrylic-nitrile, polytetrafluoroethylene, polyvinylchloride, polyvinylidene chloride, and polychlorodiene, and other copolymers thereof.

Other useful pressure-sensitive adhesives ("PSA") can include acrylic-based pressure-sensitive adhesives and silicone-based pressure-sensitive adhesives such as those described in U.S. Pat. Nos. 5,474,783, and 5,656,386. Suitable commercially available acrylic-based polymers can include adhesives that are commercially available and include the polyacrylate adhesives sold under the trademarks Duro-Tak by National Starch and Chemical Corporation, Bridgewater, N.J., such as Duro-Tak 87-2194, Duro-Tak 87-2196, Duro-Tak 87-1197, 87-4194, 87-2510, 87-2097 and 87-2852. Other suitable acrylic-based adhesives are those sold under the trademarks Gelva-Multipolymer Solution (GMS) (Monsanto; St. Louis, Mo.), such as GMS 737, 788, 1151, 3087 and 7882.

Suitable silicone-based pressure-sensitive adhesives can include those described in Sobieski et al, "Silicone Pressure Sensitive Adhesives," Handbook of Pressure-Sensitive Adhesive Technology, 2nd ed., pp. 508–517 (D. Satas, ed.), Van Nostrand Reinhold, New York (1989), incorporated by reference in its entirety. Other useful silicone-based pressure sensitive adhesives are described in the following U.S. Pat. Nos.: U.S. Pat. Nos. 4,591,622; 4,584,355; 4,585,836; and 4,655,767. Suitable silicone-based pressure-sensitive adhesives are commercially available and include the silicone adhesives sold under the trademarks BIO-PSA 7-4503, BIO-PSA 7-4603, BIO-PSA 7-4301, 7-4202, 7-4102, 7-4106, and BIO-PSA 7-4303 by Dow Corning Corporation, Medical Products, Midland, Mich.

The amount of the polymer carrier can range from 2 to 99 wt %, preferably, 30 to 90 wt %, even more preferably 40 to 80 wt %.

The pressure-sensitive adhesives can be blended to modulate the solubility of the prodrug in the carrier system such as described in the '783 patent referenced above. In a particularly preferred embodiment of the invention, the multiple polymer adhesive system comprises a pressure-sensitive adhesive blend of an acrylic-based polymer and a silicone-based polymer. The acrylic-based polymer and silicone-based polymer are preferably in a ratio by weight, respectively, from about 2:98 to about 96:4, more preferably from about 2:98 to about 90:10, and even more preferably about 2:98 to about 86:14. The amount of acrylic-based polymer (also referred to broadly as a polyacrylate) and silicone-based polymer (also referred to broadly as a polysiloxane) is adjusted so as to modify the saturation concentration of the enalapril ethyl ester or other prodrug in the binary polymer adhesive system in order to affect the rate of delivery of the enalapril ethyl ester from the transdermal drug delivery systems and through the skin. Other useful ranges include about 5–85% by weight of the acrylate-based polymer, 10–90% by weight of polyisobutylene and 5–95% by weight of silicone-based polymer.

The transdermal drug delivery system can also contain agents known to accelerate the delivery of the prodrug through the skin. These agents have been referred to as skin-penetration enhancers, accelerants, adjuvants, and sorption promoters, and are collectively referred to herein as "enhancers" and are described in U.S. Pat. No. 6,221,383. They can include polyhydric alcohols such as dipropylene glycol, propylene glycol, and polyethylene glycol which enhance the solubility of enalapril ethyl ester; oils such as olive oil, squalene, and lanolin; fatty ethers such as cetyl ether and oleyl ether; fatty acid esters such as isopropyl myristate which enhance the enalapril ethyl ester diffusibility; urea and urea derivatives such as allantoin which affect the ability of keratin to retain moisture; polar solvents such as dimethyidecylphosphoxide, methyloctylsulfoxide, dimethyllaurylamide, dodecylpyrrolidone, isosorbitol, dimethylacetonide, dimethylsulfoxide, decylmethylsulfoxide, and dimethylformamide which affect keratin permeability; salicylic acid which softens the keratin; amino acids which are penetration assistants; benzyl nicotinate which is a hair follicle opener; and higher molecular weight aliphatic surfactants such as lauryl sulfate salts which change the surface state of the skin and drugs administered. Other agents include oleic and linoleic acids, ascorbic acid, panthenol, butylated hydroxytoluene, tocopherol, tocopheryl acetate, tocopheryl linoleate, propyl oleate, and isopropyl palmitate. Particularly preferred are combinations of polyhydric alcohols such as glycerine, dipropylene glycol, butylene glycol, propylene glycol and one or more of oleyl alcohol and oleic acid.

In some embodiments, the invention can also include a plasticizer or tackifying agent and is incorporated into the formulation to improve the adhesive characteristics of the pressure-sensitive adhesive composition. Such plasticizers or tackifying agents include: (1) aliphatic hydrocarbons; (2) mixed aliphatic and aromatic hydrocarbons; (3) aromatic hydrocarbons; (4) substituted aromatic hydrocarbons; (5) hydrogenated esters; (6) polyterpenes; and (7) hydrogenated wood rosins.

The tackifying agent employed is preferably compatible with the blend of polymers. In preferred embodiments, the tackifying agent is silicone fluid (e.g., 360 Medical Fluid, available from Dow Corning Corporation, Midland, Mich.) or mineral oil. Silicone fluid is useful for blends comprising polysiloxane as a major component. In other embodiments, where a synthetic rubber, for example, is a major component, mineral oil is a preferred tackifying agent.

When the prodrug is not readily soluble in the polymer system, a co-solvent for the prodrug and polymer can be added. Co-solvents, such as lecithin, retinal derivatives, tocopherol, dipropylene glycol, triacetin, propylene glycol, saturated and unsaturated fatty acids, mineral oil, silicone fluid, alcohols, butyl benzyl phthalate, and the like are useful in the practice of the instant invention depending on the solubility of the prodrug in the multiple polymer adhesive system.

The compositions of this invention may further be provided with various thickeners, fillers and other additives known for use with transdermal drug delivery systems. For example, a soluble PVP may be blended with one or more other polymers in order to further modulate the transdermal permeation rate of the prodrug. The term "polyvinylpyrrolidone," or "PVP" refers to a polymer, either a homopolymer or copolymer, containing N-vinylpyrrolidone as the monomeric unit. Typical PVP polymers are homopolymeric PVPs and the copolymer vinyl acetate vinylpyrrolidone. The homopolymeric PVPs are known to the pharmaceutical industry under a variety of designations including Povidone, Polyvidone, Polyvidonum, Polyvidonum solubile, and Poly(1-vinyl-2-pyrrolidone). The copolymer vinyl acetate vinylpyrrolidone is known to the pharmaceutical industry as Copolyvidon, Copolyvidone, and Copolyvidonum. One class of embodiments includes binary compositions comprising a rubber-based pressure-sensitive adhesive and a soluble PVP, wherein the rubber-based pressure-sensitive adhesive is a polysiloxane. Other embodiments include ternary compositions comprising a rubber-based pressure-sensitive adhesive, a polyacrylate polymer, and a soluble PVP, wherein the rubber-based pressure-sensitive adhesive is a polysiloxane.

A device, or individual dosage unit, of the present invention can be produced in any manner known to those of skill in the art. After the dermal composition is formed, it may be brought into contact with the backing layer in any manner known to those of skill in the art. Such techniques include calender coating, hot melt coating, solution coating, and the like. Of course, backing materials are well known in the art and can comprise plastic films of polyethylene, vinyl acetate resins, ethylene/vinyl acetate copolymers, polyvinyl chloride, polyurethane, and the like, metal foils, non-woven fabric, cloth and commercially available laminates. The backing material generally has a thickness in the range of 2 to 1000 micrometers and the dermal composition is generally disposed on backing material in a thickness ranging from about 12 to 250 micrometers thick.

Suitable release liners are also well known in the art and include the commercially available products of Dow Corning Corporation designated Bio-Release® liner and Syl-off® 7610 liner. For preferred embodiments in which a polysiloxane is part of the multiple polymeric adhesive system, the release liner must be compatible with the silicone adhesive. An example of a suitable commercially available liner is 3M's 1022 Scotch Pak®. The configuration of the transdermal delivery system of the present invention can be in any shape or size as is necessary or desirable. Illustratively, a single dosage unit may have a surface area in the range of 1 to 200 cm$^2$. Preferred sizes are from 5 to 60 cm$^2$.

In a preferred method aspect of the invention where the carrier is a flexible, finite polymer, one or more polymers are blended to result in a pressure-sensitive adhesive composition, or transdermal drug delivery system adhesive system (with incorporated enalapril ethyl ester or other prodrug), which controls the delivery of the incorporated prodrug through the epidermis. In a preferred embodiment of the invention, a transdermal drug delivery system is prepared by mixing polyacrylate, polysiloxane, enalapril ethyl (or other prodrug) ester, optional enhancer(s), and tackifying agents and solvent(s) such as alcohols and others as known to those skilled in the art, if needed, then casting the mixture and removing solvent(s) by evaporation to form a film.

The order of steps, the amount of the ingredients, and the amount and time of agitation or mixing may be important process variables which will depend on the specific polymers and enhancers used in the formulation. These factors can be adjusted by those skilled in the art, while keeping in mind the object of providing a uniform product. It is believed that a number of other methods, including changing some of the order of steps, can be carried out and will give desirable results. In addition to having various shapes, the dosage units produces may come in various sizes. A surface area in the range of 1 to 200 square centimeters is contemplated, and the presently preferred sizes are: 5, 10, 15, 20, 30, 30 and 60 are centimeters.

EXAMPLES

The following specific examples are included as illustrative of transdermal delivery systems and compositions within the contemplation of the invention. These examples are in no way intended to be limiting of the scope of the invention. The weight percentages in the examples are based upon the dry weight of the system.

Preparation and Analysis of Enalapril Ethyl Ester

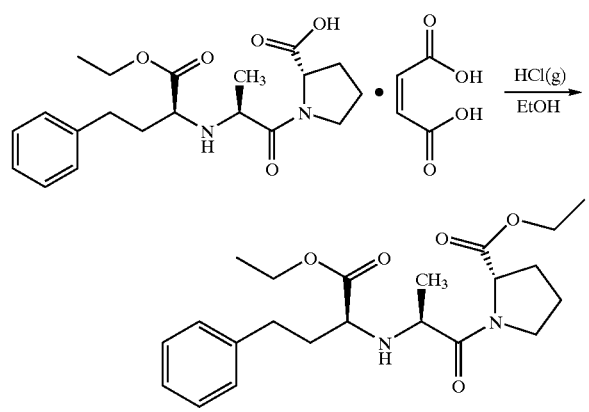

Enalapril maleate (20 g) was dissolved in 200 mL of anhydrous ethanol. Dry HCl gas was bubbled into the solution for 10 minutes. The reaction mixture was stirred at ambient temperature for overnight. The reaction mixture was refluxed for 6 hours. The solvent was evaporated in vacuo. The crude product was washed with Hexane (~50 mL) three times. The product so obtained contains primarily Enalapril Ethyl Ester HCl salt. The product was dissolved in 250 mL of water and neutralized to pH 12 (detected with pH indicator paper) with dropwise addition of 0.1 N NaOH(aq) solution. CH2Cl2 (150 mL) was used to extract the free base. The organic layer was dried over Na2SO4. The solvent was evaporated in vacuo. The product was further purified over a silica gel column using 5% methanol in CH2Cl2 as the eluant. Enalapril ethyl ester is an oil at ambient temperature. Molecular weight (C22H32N2O5, FW: 404.50) of MH$^+$ by mass spectrometry is 405. $^1$H NMR in CDCl3: 1.17–1.29 (m, 9H); 1.84 (m, 4H); 2.14(t, 2H); 2.60(m, 2H); 3.22(t, 1H); 3.47(m, 3H); 4.1(m, 4H); 4.46(t, 1H); 7.10(t, 1H); 7.12(d, 2H); 7.24(t, 2H). $^{13}$C NMR in CDCl3: 14.11, 14.29, 18.71, 24.85, 28.85, 32.01, 35.10, 46.47, 53.54, 58.86, 59.88, 60.69, 61.03, 76.83, 77.15, 77.35, 77.47, 125.90, 141.33, 171.99, 173.54, 174.31.

Preparation of Transdermal Delivery Compositions

The transdermal composition used in Example 2 below was prepared as follows: A mixture of 5.17 g of a Polysiloxane Adhesive (BIO-PSA 7-4502), 2.44 g of an Acrylate Adhesive (GMS 788), 0.25 g of Dipropylene Glycol, 0.15 g of Oleyl Alcohol and 0.50 g of Enalapril Ethyl Ester were admixed together in a vessel and placed on a roller mixer for two hours to ensure homogenous blending of the mixture. Each blend was then cast on a polyester release liner (Scotch Pak 1022; 3M: Minneapolis, Mich.) with a 15 mil wet gap applicator. The cast downs were dried for five minutes at ambient temperature under a hood and for an additional five minutes in a convection air oven at 85° C. to drive-off the volatile process solvents. Upon completion of this step, the release liner coated with the dried adhesive-drug composition was laminated to the polyester side of a polyester/ethylene vinyl acetate backing material (Scotch Pak 1012). The method of Example 2 was used with the appropriate amounts of starting materials to yield compositions having the following concentrations on a dry basis (i.e., after removal of the volatile solvents) set forth below together with Examples 1 and 3.

TABLE I

| Component (wt % dry) | Ex. 1 | Ex. 2 | Ex. 3 |
|---|---|---|---|
| Acrylate Adhesive (GMS 788) | 20 | 20 | 20 |
| Polysiloxane Adhesive (BIO-PSA ® 7-4502) | 67 | 62 | 57 |
| Dipropylene Glycol (BIO-PSA ® 7-4102) | 5 | 5 | 5 |
| Oleyl Alcohol | 3 | 3 | 3 |
| Enalapril Ethyl Ester | 5 | 10 | 15 |
|  | 100 | 100 | 100 |

"BIO-PSA 7-4502 is a trademark of DOW CORNING CORPORATION, MEDICAL PRODUCTS, Midland, Mich. for polysiloxane adhesives in organic solutions."

"Gelva-Multipolymer Solution (GMS) 788 is a trademark of SOLUTIA, INC. Springfield, Mass., for polyacrylate adhesives in organic solutions."

Flux Evaluation

Human cadaver skin permeation studies were performed to quantitatively determine the effective permeation of enalapril ethyl ester through the stratum corneum. The stratum corneum was obtained from split thickness, cryopreserved cadaver skin by the heat separation technique (~55°). Samples of 5/16" diameter were cut from the laminate, in triplicate, and mounted onto ½" cut pieces of the stratum corneum. These samples were then placed on modified Franz diffusion cells. The receptor was filled with 7.5 mL of 0.9% NaCl and 0.01% NaN3 in deionized water. The cells were maintained at a constant 32° C. and were magnetically stirred at approximately 300 rpm. At specified time points, samples of the receptor phase were taken with complete replacement of the receptor phase. These samples were quantified by high-performance liquid chromatography (HPLC) utilizing Waters HPLC instrumentation. C-8(15 cm×4.6 mm) 5 μm particle size columns (HYPERSIL made by MetaChem Technologies, Inc.; Torrance, Calif.) were used at 50° C. (column temperature). The mobile phase contained 50% acetonitrile: 50% buffer (10 mM KH2PO4, pH=2.7). The detection wavelength was 214 nm. HPLC flow rate is 1.5 mL/min.

| Example | Average Flux/hr |
|---|---|
| 1 | 1.4 μg/cm$^2$ |
| 2 | 3.9 μg/cm$^2$ |
| 3 | 8.3 μg/cm$^2$ |

Figure 2:
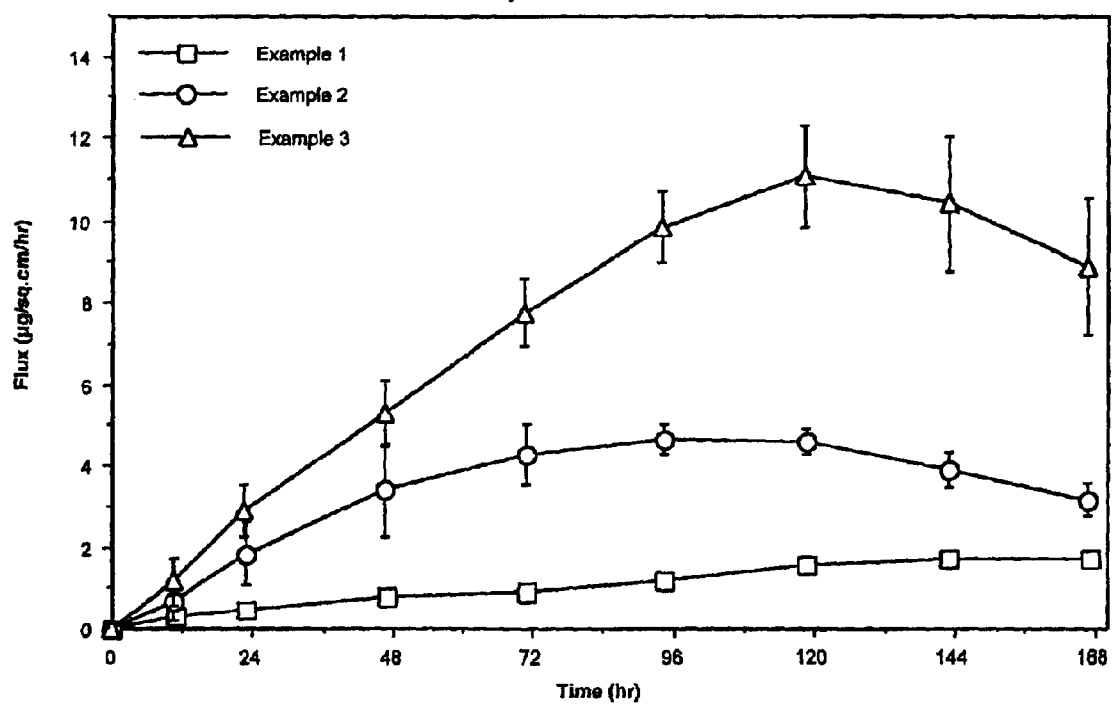
FIG. 2 shows the in vitro flux of enalapril ethyl ester in varying concentrations from a transdermal adhesive composition of the present invention.

FIG. 2 shows the in vitro flux of enalapril ethyl ester in varying concentrations from a transdermal adhesive composition of the present invention. The in vitro flux of enalapril ethyl ester from the formulation of Example 2 (but tested with different cadaver skin) as compared to enalapril maleate in the same carrier composition is shown in FIG. 1 as circles ("○") and squares ("□"), respectively.

It was found that the ethyl ester group on the proline moiety of enalapril ethyl ester was selectively hydrolyzed by an esterase enzyme in the skin. More than 50% of the penetrated enalapril ethyl ester was hydrolyzed into enalaprilat after permeation through the skin.

While these preferred embodiments of the present invention have been described, it should be readily apparent to a person of skill in the art that various changes, adaptations, and modifications may be made therein without departing from the spirit of the invention and the scope of the appended claims.

What is claimed is:

1. A method of transdermally administering a therapeutically effective amount of enalaprilat through the skin of a patient, said method comprising the steps of:
   a) applying to the skin of said patient a dermal composition comprising a therapeutically effective amount of enalapril ethyl ester in admixture with a pharmaceutically acceptable carrier; and
   b) maintaining said dermal composition in contact with said skin for a time sufficient to deliver a therapeutically effective amount of enaliprilat,
said method characterized in that the flux of enalapril ethyl ester is greater than that of enalapril maleate.

2. The method according to claim 1 wherein the flux of enalapril ethyl ester and the flux of enalapril maleate are in a ratio of 100:1 to 3:1.

3. The method according to claim 2 wherein said ratio is 70:1 to 10:1.

4. The method according to claim 1 wherein said carrier comprises a pressure-sensitive adhesive.

5. The method according to claim 4 wherein said pressure-sensitive adhesive is a polymer or a mixture of a plurality of polymers.

6. The method according to claim 1 wherein said carrier is a flexible, finite polymer that comprises a least one of an acrylic-based polymer and a silicon-based polymer.

7. The method according to claim 1 wherein said dermal composition further comprises an enhancer.

8. The method according to claim 7 wherein said enhancer comprises dipropylene glycol and oleyl alcohol.

* * * * *